(12) United States Patent
Chen et al.

(10) Patent No.: US 10,289,699 B2
(45) Date of Patent: May 14, 2019

(54) VEHICLE INSPECTION METHODS AND SYSTEMS

(71) Applicants: Tsinghua University, Beijing (CN); Nuctech Company Limited, Beijing (CN)

(72) Inventors: Zhiqiang Chen, Beijing (CN); Li Zhang, Beijing (CN); Ziran Zhao, Beijing (CN); Yaohong Liu, Beijing (CN); Jianping Gu, Beijing (CN); Zheng Hu, Beijing (CN); Qiang Li, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 60 days.

(21) Appl. No.: 15/282,134

(22) Filed: Sep. 30, 2016

(65) Prior Publication Data

US 2017/0017667 A1 Jan. 19, 2017

Related U.S. Application Data

(63) Continuation of application No. PCT/CN2015/098438, filed on Dec. 23, 2015.

(30) Foreign Application Priority Data

Dec. 30, 2014 (CN) .......................... 2014 1 0840660

(51) Int. Cl.
 *G06K 9/00* (2006.01)
 *G06F 17/30* (2006.01)
 (Continued)

(52) U.S. Cl.
 CPC ....... *G06F 17/30256* (2013.01); *G01N 23/04* (2013.01); *G06F 17/30274* (2013.01);
 (Continued)

(58) Field of Classification Search
 CPC ............. G01V 5/0008; G06K 2209/23; G06K 2209/09; G06T 2207/10116;
 (Continued)

(56) References Cited

U.S. PATENT DOCUMENTS 5,031,228 A * 7/1991 Lu ...................... G06K 9/00221
   348/E17.001
5,987,159 A * 11/1999 Nichani ................. G01N 21/88
   382/141

(Continued)

FOREIGN PATENT DOCUMENTS

CN    101162204 A    4/2008
CN    103338325 A    10/2013
(Continued)

OTHER PUBLICATIONS

English translation of CN101162204, 2008.*
(Continued)

*Primary Examiner* — Li Liu
(74) *Attorney, Agent, or Firm* — Knobbe, Martens, Olson & Bear, LLP

(57) ABSTRACT

A vehicle inspection method and system are disclosed. In one aspect, the method includes acquiring a transmission image of an inspected vehicle. The method further includes acquiring a transmission image template of a vehicle model corresponding to the model of the inspected vehicle from a database. The method further includes performing registration on the transmission image of the inspected vehicle and the transmission image template. The method further includes determining a difference between a transmission image after the registration and a transmission image template after the registration, to obtain a difference area of the transmission image of the vehicle relative to the transmission image template. The method further includes processing the difference area to determine whether the vehicle
(Continued)

carries a suspicious object or not. In some embodiments, this solution can avoid the problems of a detection loophole and a poor effect of manually determining an image in a conventional manner, and is important to assist the security inspection for small vehicles.

8 Claims, 3 Drawing Sheets

(51) Int. Cl.
*G01N 23/04* (2018.01)
*G06T 7/00* (2017.01)
*G06T 7/33* (2017.01)
*G06K 9/42* (2006.01)
*G06K 9/62* (2006.01)

(52) U.S. Cl.
CPC .............. *G06T 7/001* (2013.01); *G06T 7/337* (2017.01); *G01N 2223/401* (2013.01); *G01N 2223/631* (2013.01); *G06K 9/42* (2013.01); *G06K 9/6215* (2013.01); *G06K 2209/09* (2013.01); *G06K 2209/23* (2013.01); *G06T 2207/10116* (2013.01); *G06T 2207/30268* (2013.01)

(58) Field of Classification Search
CPC ........... G06T 2207/30248; G06T 7/001; G06T 2207/30112
See application file for complete search history.

(56) References Cited

U.S. PATENT DOCUMENTS

| | | | |
|---|---|---|---|
| 6,047,041 A | 4/2000 | Ellinger | |
| 9,824,453 B1* | 11/2017 | Collins | ................ G06T 7/0075 |
| 2005/0267657 A1* | 12/2005 | Devdhar | ............ G06K 9/00208 |
| | | | 701/33.4 |
| 2006/0257005 A1* | 11/2006 | Bergeron | ............... G01N 23/04 |
| | | | 382/103 |
| 2008/0136625 A1* | 6/2008 | Chew | ................... G01V 5/0008 |
| | | | 340/540 |
| 2009/0220156 A1* | 9/2009 | Ito | ...................... G06K 9/00248 |
| | | | 382/201 |
| 2009/0290757 A1* | 11/2009 | Mian | .................. G06K 9/00214 |
| | | | 382/104 |
| 2012/0076263 A1* | 3/2012 | Hayes | .................. G01V 5/0008 |
| | | | 378/57 |
| 2014/0270383 A1* | 9/2014 | Pederson | ......... G08B 13/19647 |
| | | | 382/104 |
| 2015/0117602 A1* | 4/2015 | Chen | .................... G01V 5/0058 |
| | | | 378/41 |
| 2015/0143913 A1* | 5/2015 | Adams | ................ G01N 33/227 |
| | | | 73/655 |
| 2015/0324885 A1* | 11/2015 | Griffin | ............... G06Q 30/0643 |
| | | | 705/26.5 |
| 2015/0369955 A1* | 12/2015 | Al-Hoshani | ......... G01V 5/0016 |
| | | | 378/57 |
| 2016/0178790 A1 | 6/2016 | Li et al. | |
| 2017/0097944 A1* | 4/2017 | Bhanu | ............... G06F 17/30256 |
| 2017/0299765 A1* | 10/2017 | Parikh | .................. G01V 5/0083 |

FOREIGN PATENT DOCUMENTS

| | | |
|---|---|---|
| CN | 103984961 A | 8/2014 |
| EP | 3035087 A1 | 6/2016 |

OTHER PUBLICATIONS

International Search Report for Application No. PCT/CN2015/098438 dated Feb. 14, 2016.
European Search Report for European Application No. 157875152.9, dated Oct. 9, 2017 in 8 pages.

* cited by examiner

VEHICLE INSPECTION METHODS AND SYSTEMS

CROSS-REFERENCE TO RELATED APPLICATIONS

This application claims priority to International Application No. PCT/CN2015/098438, filed on Dec. 23, 2015, entitled "VEHICLE CHECKING METHOD AND SYSTEM," Chinese Application No. 201410840660.0, filed on Dec. 30, 2014, incorporated herein by reference in their entity.

BACKGROUND

Field

The disclosed technology relates to automatically detecting suspicious objects in a radiation image, and in particular, to security inspection methods and devices for inspecting and identifying prohibited dangerous goods and suspicious objects in a vehicle scanning system.

Description of the Related Technology

Currently, as the severity and frequency of terrorist attacks are becoming increasingly more prevalent, security inspection is becoming vital to the security and safety of our friends and family. Cars are often used as a carrier to smuggle illegal goods and carry out criminal activities as a result of simple implementations and low costs that are required, and the difficulty of catching such criminals. For example, criminal activities such as activities related to narcotics, smuggling, explosives, and the like often occur. There is an imminent need to improve the reliability of security inspection for vehicles.

Existing intelligent vehicle security inspections are mainly performed using X-ray detection and vehicle chassis detection. A chassis security inspection system utilizes a digital camera for photographing the chassis to determine whether there is an item hidden inside the chassis or by looking for visible characteristics of images of the chassis. Security inspection for the vehicle's internal compartments are performed manually by using a detector, which complicates ease of operation and is not an efficient method, thereby resulting in a slow and inaccurate inspection for vehicles. There is a need for using X-ray technology to generate a transmission image, or transmission x-ray image, that penetrates the entire vehicle, which can be used to assist security personnel to identify suspicious objects depending on a variety of X-ray images.

Many problems arise in this field of technology, such as a clustering of goods within the vehicle, different styles and shapes of suspicious objects, and sophisticated structures for a myriad of different vehicle structure types.

SUMMARY OF CERTAIN INVENTIVE ASPECTS

The disclosed technology includes a vehicle inspection method and system. In some embodiments, the vehicle inspection method and system can improve the efficiency and accuracy of vehicle inspection.

The disclosed technology includes a vehicle inspection method. The method includes acquiring a transmission image of an inspected vehicle. The method further includes acquiring a transmission image template of a vehicle model corresponding to the model of the inspected vehicle from a database. The method further includes performing registration on the transmission image of the inspected vehicle and the transmission image template. The method further includes determining a difference between a transmission image after the registration and a transmission image template after the registration. The method further includes obtaining a difference area of the transmission image of the vehicle relative to the transmission image template. The method further includes processing the difference area to determine whether the vehicle carries a suspicious object or not.

In some embodiments, acquiring a transmission image template of a vehicle model corresponding to the model of the inspected vehicle from a database includes retrieving the transmission image template of the vehicle model from the database based on a unique identifier of the inspected vehicle.

In some embodiments, acquiring a transmission image template of a vehicle model corresponding to the model of the inspected vehicle from a database includes extracting information on an internal structure of the vehicle from the transmission image. In some embodiments the method includes retrieving the transmission image template of the vehicle model from the database based on the information on the internal structure as well as information on external features of the vehicle.

In some embodiments, performing registration on the transmission image of the inspected vehicle and the transmission image template includes: performing rigid registration on the transmission image of the inspected vehicle and the transmission image template to have global transformation and alignment on the image. In some embodiments, the method includes performing elastic registration on the transmission image of the inspected vehicle and the transmission image template to eliminate local deformation.

In some embodiments, performing rigid registration includes: performing feature extraction on two images to obtain feature points. In some embodiments, the method includes finding a pair of matched feature points through similarity measurement. In some embodiments, the method includes obtaining image spatial coordinate transformation parameters based on the pair of matched feature points. In some embodiments, the method includes performing image registration on the image spatial coordinate transformation parameters.

In some embodiments, the method further includes: performing normalization on gray levels of two images after rigid registration, before elastic registration.

In some embodiments, the method further includes: removing parts of the transmission image that are outside the image of the vehicle.

In some embodiments, the method further includes: marking the suspicious object in the difference area.

The disclosed technology includes a vehicle inspection system. In some embodiments, the system includes a radiation image system configured to acquire a transmission image of an inspected vehicle. In some embodiments, the system further includes an image processing unit configured to acquire a transmission image template of a vehicle model corresponding to the model of the inspected vehicle from a database, perform registration on the transmission image of the inspected vehicle and the transmission image template, determine a difference between a transmission image after the registration and a transmission image template after the registration to obtain a difference area of the transmission image of the vehicle relative to the transmission image template, and process the difference area to determine whether the vehicle carries a suspicious object or not.

The disclosed technology includes an image processing unit. In some embodiments, the image processing unit is configured to: extract information on an internal structure of the vehicle from the transmission image; and retrieve the transmission image template of the vehicle model from the database based on the information on the internal structure as well as information on external features of the vehicle.

The solutions according to the above embodiments of the disclosed technology perform inspection for a suspicious object based on a scanned image of a vehicle. This can avoid the problems of a detection loophole and a poor effect of manually determining an image in a conventional manner, and is important to assist the security inspection for small vehicles.

BRIEF DESCRIPTION OF THE DRAWINGS

To understand the disclosed technology in a better way, a detailed description of the disclosed technology will be given with reference to the following drawings, in which.

DETAILED DESCRIPTION OF CERTAIN EMBODIMENTS

Figure 1:
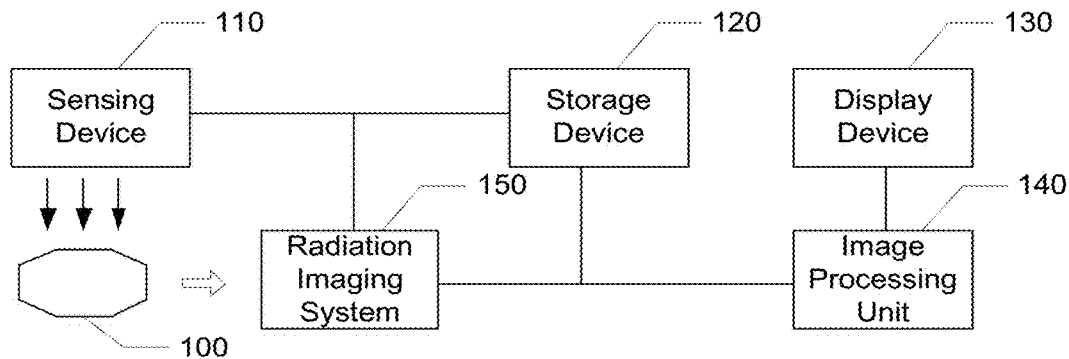
FIG. 1 is a schematic diagram illustrating a vehicle inspection system according to an embodiment of the disclosed technology.

Specific embodiments of the disclosed technology will be described in detail below. It should be noted that the embodiments herein are used for illustration only, without limiting the disclosed technology. Hereinafter, to provide a thorough understanding of the disclosed technology, numerous specific details are set forth. However, it would be obvious for one ordinarily skilled in the art that the disclosed technology can be practiced without these specific details. In other examples, known structures, materials, or methods are not described in detail to avoid any possible obfuscation of the disclosed technology.

Throughout the specification, the reference to "one embodiment," "an embodiment," "one example" or "an example" means that the specific features, structures or properties described in conjunction with the embodiment or example are included in at least one embodiment of the disclosed technology. Therefore, the phrases "in one embodiment," "in an embodiment," "in one example" or "in an example" presented in various positions throughout the specification may not necessarily refer to the same embodiment or example. Furthermore, specific features, structures or properties may be combined into one or more embodiments or examples in any appropriate combination and/or sub-combination. Moreover, it should be understood for those skilled in the art that the term "and/or" used herein means any and all combinations of one or more listed items.

In view of the low inspection efficiency and accuracy, an embodiment of the disclosed technology proposes a vehicle inspection method. According to the method, after acquiring a transmission image of an inspected vehicle, a transmission image template of a vehicle model corresponding to the model of the inspected vehicle is acquired from a database. Then, registration is performed on the transmission image of the inspected vehicle and the transmission image template, and a difference between a transmission image after the registration and a transmission image template after the registration is determined to obtain a difference area of the transmission image of the vehicle relative to the transmission image template. Finally, the difference area is processed to determine whether the vehicle carries a suspicious object or not. This solution can eliminate false detection caused by the imaging environments.

In addition, according to other embodiments, not only rigid registration but also elastic registration may be done. This can eliminate three-dimension deformation, thereby resulting in the more accurate registration for template images and images to be inspected. Similarly, in some embodiments, a difference image is processed in a special manner, thereby overcoming the false detection caused by three-dimension deformation of suspicious objects and goods as well as scanning noises and the like.

In some embodiments, the energy or dose of devices for generating images to be detected and template images may be defined to be the same, as much as possible, so that the image noise is low and the image deformation is small. The stricter this condition is, the better the effect of image subtraction will become. In addition, the noise is limited within a certain range. Two images to be detected are pro-processed and then are aligned by means of rigid registration. The three-dimension deformation may be reduced by further using elastic registration. Thereafter, a difference image is post-processed to distinguish entrained items from goods and objects that are mistakenly inspected due to three-dimension deformation, scanning noise, etc. Finally, entrained items are presented in the result.

FIG. 1 is a schematic diagram illustrating a vehicle inspection system according to an embodiment of the disclosed technology. As shown in FIG. 1, the vehicle inspection system according to the embodiment of the disclosed technology performs automatic security inspection for a vehicle by utilizing its transmission images.

The system as illustrated in FIG. 1 includes a sensing device 110, a radiation image system 150, a storage device 120, an image processing unit 140 and a display device 130.

In some embodiments, the sensing device 110 includes one or more sensors such as a Charge-coupled Device (CCD) device for obtaining information on the vehicle's former face and information on exterior dimensions of the vehicle, etc. In other embodiments, the sensing device 110 may include a camera for capturing an image of the inspected vehicle's plate number and an identifying unit for identifying the inspected vehicle's plate number from the image. In another embodiment, the sensing device 110 includes a reader for reading the inspected vehicle's ID from a RF label carried by the vehicle.

The radiation imaging system 150 performs X-ray scanning on the inspected vehicle to obtain an X-ray image of the inspected vehicle. The storage device 120 stores the X-ray image and a vehicle model template database. The vehicle model template database stores a transmission image template and the like.

The image processing unit 140 retrieves a vehicle model corresponding to the vehicle from the vehicle model template database and determines a difference area of the transmission image relative to the transmission template image. The display device 130 presents the difference area to the user.

For example, when there is a small vehicle to be inspected, the sensing device 110 obtains an image of the vehicle's plate. The sensing device 110 may also identify the corresponding small vehicle, and generates a unique identification ID such as a plate number for the small vehicle in connection with a software system. The unique identification ID is a unique identification, with which the small vehicle can pass the software system. The identification ID may be either data generated by the software system for the small vehicle or a plate number of the vehicle. The present software system identifies a vehicle through its plate number.

As an example, the data processing unit 140 retrieves the template library by using the plate number to obtain a template image corresponding to the small vehicle to be inspected. Then, a difference area of the obtained transmission image relative to the template image is determined. The display device 130 presents the difference area to the user.

Figure 2:
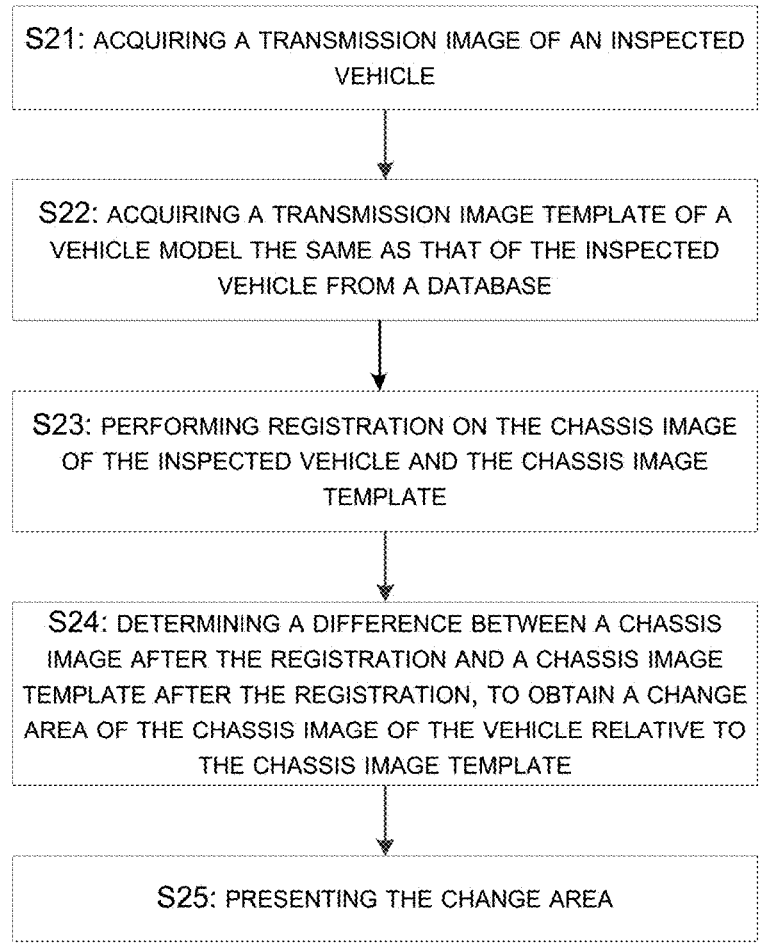
FIG. 2 is a flow chart of a vehicle inspection method according to an embodiment of the disclosed technology.

In the following, a flow chart of a vehicle inspection method according to an embodiment of the disclosed technology will be further explained by referring to FIG. 2. FIG. 2 illustrates the flow chart of the vehicle inspection method according to an embodiment of the disclosed technology.

At step S21, a transmission image of an inspected vehicle is acquired. At step S22, a transmission image template of a vehicle model corresponding to the model of the inspected vehicle is acquired from a database.

Since different scanning devices have X-ray sources of different energy or doses and detectors of different sizes, scanning the same vehicle by using different scanning devices may lead to different radiation images. In view of this, an embodiment of the disclosed technology preferably selects two radiation images of the same device as input images (including an image of the inspected vehicle to be detected and the retrieved template image of the empty vehicle). The image to be detected may be generated by the device in real-time. There are a variety of approaches to acquire the template image, for example, manually or automatically. The approaches may include, but not limited to: (1) plate number matching, in which a historical vehicle model image library is searched for the last image of the vehicle as a template; (2) vehicle information manual search, in which a matched model is searched in the standard vehicle model image library through vehicle information in the image to be detected (for example, vehicle model, years since the vehicle was purchased, high-end or low-end configuration, etc.), and an input is manually entered; and (3) vehicle model automatic identification, in which an algorithm is employed to automatically search the standard vehicle model image library based on features of the image to be detected to automatically acquire the template.

As an example, information on the vehicle's internal structure may be extracted from a transmission image, which is obtained through scanning, and then the transmission image template of the vehicle model may be retrieved from the database based on the information on the internal structure as well as information on external features of the vehicle.

Then, the transmission image may be selectively pre-proposed. Since a resolution of a radiation image depends on the corresponding scanning device and different small vehicles have different lengths and widths, there are usually different air areas around the vehicle in the scanned images. In addition to the efficiency of the algorithm, these air areas may influence the algorithm's effects with noises therein. The embodiment of the disclosed technology may perform pro-processing on the image in two steps including cutting the vehicle and down sampling.

The cutting mainly depends on edge information. In particular, this may be done by determining a location of the vehicle in the image by means of some necessary de-noising and enhancement and then taking the smallest rectangle where the vehicle is presented as a sub-image for the subsequent processing.

Figure 3:
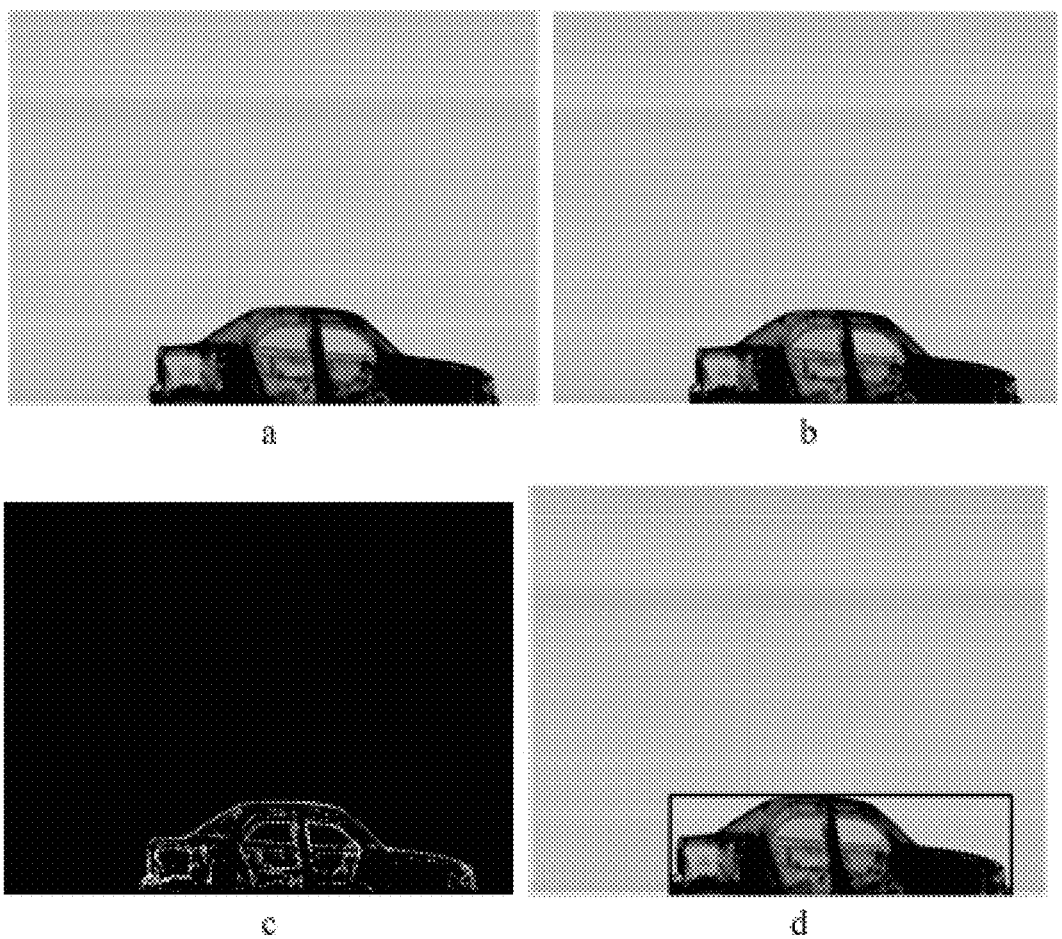
FIG. 3 is a schematic diagram illustrating cutting an image of a vehicle in the vehicle inspection method according to an embodiment of the disclosed technology.

FIG. 3 shows a schematic diagram illustrating the cutting. In order to achieve robustness, the cutting may be carried out in three steps. First of all, strip removal is performed to obtain an image having a slightly changing background. Secondly, an image gradient is solved and a gradient map is quantized to remove influence of the small gradient fluctuations. Thirdly, the largest continuous region in the horizontal and vertical projections (i.e., the largest location of the vehicle) may be obtained in a binary quantized gradient map. The strip removal may be done by performing strip removal in the horizontal and vertical directions, respectively. This will be illustrated by assuming, for example, the strip removal in the horizontal direction. In this case, a projection sequence Proj of the image in the vertical direction may be obtained. Then, median filtering is applied on Proj, a strip may be determined as having a large different between before the filtering and after the filtering, and values in the line of the strip are replaced with values in the closest non-strip image line. The gradient may be solved by performing quantization on the image (for example, the quantization may have a level of about 8) and solving the gradient on the quantized image to obtain the image as illustrated in c of FIG. 3. The location of the vehicle may be determined by obtaining projections in the horizontal and vertical directions from the gradient map and obtaining the largest continuous region after subtracting the smallest values from the projections in the horizontal and vertical directions, respectively (i.e., removing the possible strip influences). This region is the location of the vehicle. The result of the cutting is illustrated in d of FIG. 3.

When the size of an image is still too larger after the cutting, the down sampling may be used to further reduce the size of the image. An embodiment of the disclosed technology uniformly scale the size of the image to 1024 pixels, and the width may be scaled in the same scaling as that of the length. According to this embodiment, the time for running the algorithm for the image of such a size may be within 2 seconds, which substantially implements real-time.

At step S23, registration is performed on the transmission image of the inspected vehicle and the transmission image template. Since there is a certain degree of rotation, displacement, geometric deformation and the like difference in the image to be detected and the template image, it is evidently necessary to align these two images before comparing them. According to an embodiment of the disclosed technology, automatic registration is done by firstly substantially aligning the images by means of rigid registration in terms of size and displacement, then performing gray amplitude normalization to adjust gray levels of the images to a unified range, and then applying elastic registration to perform the finer non-linear registration on the two images, so as to eliminate the effects such as the three-dimension formation.

The rigid registration is to perform global transformation and alignment on images. This may be done by performing feature extraction on two images to obtain feature points, finding a pair of matched feature points through similarity measurement, then obtaining image spatial coordinate transformation parameters based on the pair of matched feature points, and finally performing image registration on the image spatial coordinate transformation parameters. The feature extraction is the key of the registration, and the proper feature extraction may ensure success of feature matching. It is important for the matching precision to seek for a feature extraction method having good invariance and accuracy. There are many feature extraction methods, and it would be appreciated that many alternative algorithms may be contemplated for these feature extraction methods, for example, the typical Scale Invariant Feature Transform (SIFT) algorithm, Smallest Univalue Segment Assimilating Nucleus (SUSAN) algorithm, Harris corner detector, Speed Up Robust Feature (Surf) algorithm, etc. Preferably, an embodiment of the disclosed technology employs SIFT algorithm in feature extraction.

Figure 4:
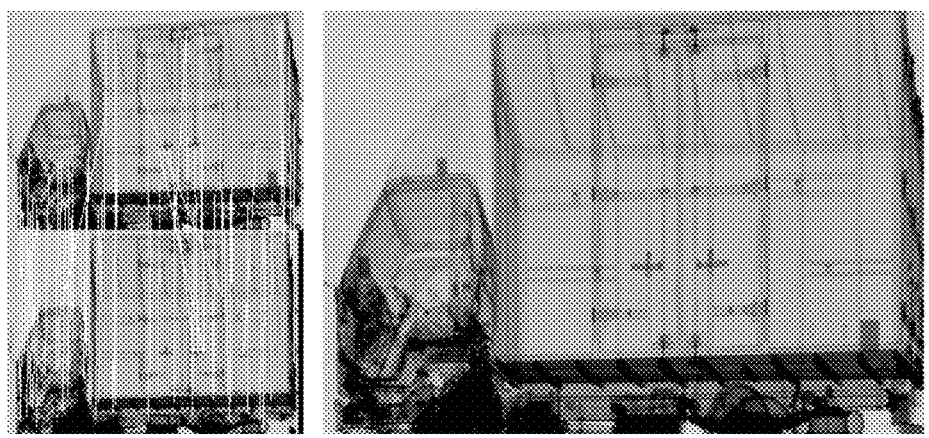
FIG. 4 is a schematic diagram illustrating registration of an image of a vehicle in the vehicle inspection method according to an embodiment of the disclosed technology.

This step is to deform the image to be detected relative to the template image in terms of corresponding parameters, in such a manner that the two images are basically aligned in terms of rotation and displacement. First of all, the SIFT algorithm is sued to extract features in the images, and then deformation parameters are determined by using the Random Sample Consensus (RANSAC) algorithm. FIG. 4 illustrates effects of the algorithm. The left part of FIG. 4 shows correspondences of SIFT features points of the image to be detected and the template image. As illustrated in the right part of FIG. 4, the image after the SIFT transformation is basically aligned with the left lower template image, so that the elastic registration algorithm may be further used.

The possible different gray ranges of the two images may influence a result of the registration. In this case, normalization may be applied on the gray of the images to scale it within for example 0 to 255. During the normalization, a certain degree of enhancement may be done to increase contrast of the images.

The elastic registration on images is mainly to perform the precise registration on the images to remove the local deformation. The elastic registration may be mainly divided into two categories, i.e., a pixel based manner and a feature based manner. After comparisons in terms of computations, validity and the like, the embodiment of the disclosed technology preferably chooses the Demons elastic registration algorithm to complete this step.

At step S24, a difference between a transmission image after the registration and a transmission image template after the registration is determined, so as to obtain a difference area of the transmission image of the vehicle relative to the transmission image template.

A difference image may be obtained by determining the difference of the images after registration of the image to be detected and the template image. With the influence of the noise, each part having a difference image larger than zero may be caused by four cases, i.e., entrained items, deformation and variation of goods and the vehicle, and the other noise. The pose-processing is intended to separate entrained items in these four cases to obtain the final result. There are a variety of manners for pose-processing the difference image, for example, merging multiple difference images in connection with the size and amplitude of the area by involving a dual energy detection device, partitioning areas of interest in connected with user interactions, determining compositions based on atomic numbers of matters, etc. The parameters may be either defined by human or acquired through machine learning.

At step S25, the difference area is processed to determine whether the vehicle carries a suspicious object or not.

Figure 5:
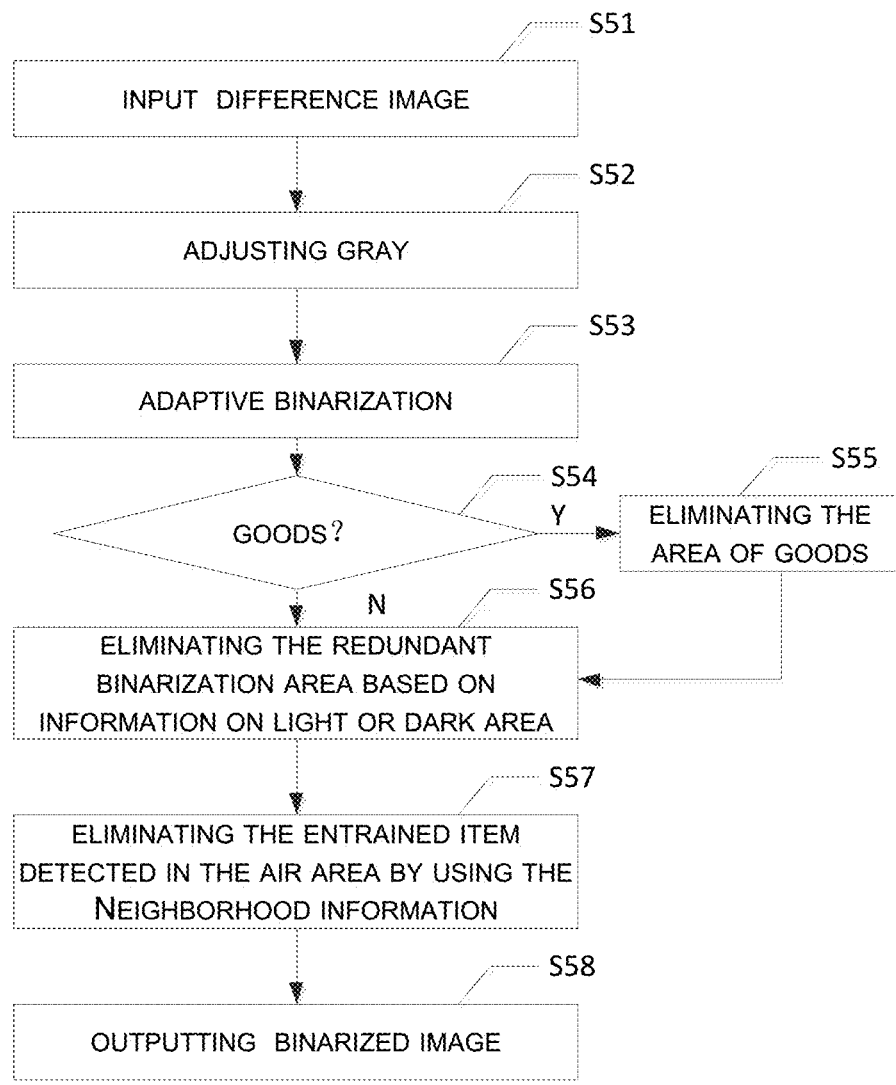
FIG. 5 is a schematic diagram illustrating processing a difference image in the vehicle inspection method according to an embodiment of the disclosed technology.

FIG. 5 illustrates processing of the difference image. At step S51, the difference image is input, and then gray adjustment is performed at step S52. Since there is a significant difference between global gray values of the input image and the template image (except for the possible entrained items), the algorithm utilizes air gray information of the two images to eliminate bad influence caused by such a difference, thereby facilitating proper binarization.

At step S53, the binarization is implemented by adaptively iteration. The possible minimum value of a binarization threshold may be determined based on a histogram of the interpolation image. The binarization is performed successively in an iterative manner by excluding influences of goods. This can ensure that the entrainment area will not be missed or mistakenly inspected.

At step S54, it is determined whether there is an area of goods, so as to remove the area if any. If yes, the area of goods is removed at step S55. In this way, goods determination may be made for the initially provided binary image to exclude the area of goods firstly, thereby facilitating inspection on the real entrained items.

At step S56, the false binarization area is eliminated. Since the actually collected images may have space rotation distortion and the like factor, the binarization area at this time may be a false area caused by rotation distortion. By utilizing the fact that there are pairs of light and dark areas in the false area, the algorithm applies a deletion on this area, so as to reduce false detection.

At step S57, the binarized image area is eliminated from the air area. For reasons at the detector and the like, the collected image may become lighter or darker row by row or become lighter or darker column by column, or may irregularly vary between light and dark. In this way, there is a significant difference of the irregular change in gray levels of the images to be detected and the template images in the air area, so that detected items may occur in the air area in the binarized image. The algorithm utilizes neighborhood information of the binarized area and the related air threshold knowledge to perform elimination processing on the obvious fake information in this area. At step S58, the binarized image is outputted.

Moreover, the other embodiments may mark, in the image to be detected, a location of a suspicious object detected by the algorithm, so as to facilitate observations by people. For example, the suspicious object' boundary may be marked by using a curve of a specified color. Alternatively, all pixels in the area of the suspicious object may be directly colored.

Although some embodiments of the disclosed technology are implemented through the above steps in such a manner that a vehicle can be inspected, it would be appreciated that each step may be implemented in multiple algorithms and is not limited the above specific description.

The above detailed description has already set forth numerous embodiments of the methods and systems for inspecting a vehicle with reference to the diagrams, flow charts, and/or examples. In the case where the diagrams, flow charts, and/or examples includes one or more functions and/or operations, one skilled in the art should appreciate that each function and/or operation in the diagrams, flow charts, or examples may be implemented by various structures, hardware, software, firmware or any combination thereof either alone and/or in any combination. In an embodiment, several parts of the subject matter described in the embodiments of the disclosed technology may be implemented by Application Specific Integrated Circuit (ASIC), Field Programmable Gate Array (FPGA), Digital Signal Processor (DSP), or any other integrated form. However, one skilled in the art should appreciate that some aspects of the embodiment disclosed herein may be partially or wholly implemented in an integrated circuit effectively, implemented as one or more computer programs running on one or more computers (for example, one or more programs running on one or more computer systems), implemented as one or more programs running on one or more processors (for example, one or more programs running on one or more micro-processors), implemented as firmware, or substantially any combination thereof, and one skilled in the art is capable to design the circuit and/or write software and/or firmware code. Further, one skilled in the art would appreciate that the mechanism of the subject matter of the disclosed technology may be distributed in various forms of program products, and the exemplary embodiments of the subject matter of the disclosed technology may be applicable irrespective of the specific types of signal carrier media for distribution. Examples of the signal carrier media include but not limited to: a recordable medium such as floppy disk, hard drive, compact disk (CD), digital versatile disk (DVD), digital tape, computer memory, etc.; and a transmission medium, such as digital and/or analog communication medium (for example, optical fiber, waveguide, wired communication link, wireless communication link, etc.)

Although the disclosed technology is already described with reference to several typical embodiments, it is to be appreciated that the terms used herein are illustrative and exemplary, rather than limiting. Since the disclosed technology may be practice in multiple forms without departing from the spirit or essence, it is to be noted that the above embodiments are not limited to any previously described details and shall be interpreted broadly within the spirit and scope defined by the claims. Therefore, all changes and variations fall into the scope of the claims or their effectives shall be embraced by the claims.

The previous description of the disclosed examples is provided to enable any person skilled in the art to make or use the present invention. Various modifications to these examples will be readily apparent to those skilled in the art, and the generic principles defined herein may be applied to other examples without departing from the spirit or scope of the invention. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope. Thus, the present invention is not intended to be limited to the examples shown herein but is to be accorded the widest scope consistent with the principles and novel features disclosed herein.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

We claim:

1. A vehicle inspection method comprising:
    acquiring a transmission image of vehicle;
    removing parts of the transmission image that are outside an inspected vehicle in the transmission image to obtain a transmission image of the inspected vehicle;
    acquiring from a database a transmission image template of a vehicle model that is the same as that of the inspected vehicle;
    performing registration on the transmission image of the inspected vehicle with the transmission image template to obtain a registered transmission image;
    determining a difference between the registered transmission image and the transmission image template, to obtain a change area of the transmission image of the vehicle relative to the transmission image template; and
    processing the change area to determine whether the vehicle carries a suspected object;
    wherein the removing parts of the transmission image comprises:
        removing strip in the transmission image of the vehicle to obtain an image having a changing background;
        obtaining a gradient map for the image having the changing background and quantizing the gradient map to obtain a binary quantized gradient map;
        obtaining a largest continuous region in a horizontal projection and a vertical projection in the binary quantized gradient map; and
        removing parts outside the largest continuous region in the transmission image of the vehicle to obtain the transmission image of the inspected vehicle, and wherein the method is performed by at least one processor.

2. The vehicle inspection method according to claim 1, wherein said acquiring from a database a transmission image template of a vehicle model that is the same as that of the inspected vehicle comprises:
    retrieving the transmission image template of the vehicle model from the database based on a unique identifier of the inspected vehicle.

3. The vehicle inspection method according to claim 1, wherein said acquiring from a database a transmission image template of a vehicle model that is the same as that of the inspected vehicle comprises:
    extracting information on an internal structure of the vehicle from the transmission image, and retrieving the transmission image template of the vehicle model from the database based on the information on the internal structure as well as information on external features of the vehicle.

4. The vehicle inspection method according to claim 1, wherein said performing rigid registration comprises:
    performing feature extraction on the transmission image and the transmission image template to obtain feature points;
    finding a pair of matched feature points through similarity measurement;

obtaining image spatial coordinate transformation parameters based on the pair of matched feature points; and performing image registration on the image spatial coordinate transformation parameters, and wherein said performing elastic registration comprises:

performing non-linear registration on the transmission image and the transmission image template so as to reduce the effects of three dimensional deformation by removing local deformation, wherein the elastic registration is pixel based and feature based.

5. The vehicle inspection method according to claim 1, further comprising:

marking the suspected object in the change area.

6. A vehicle inspection system, comprising a processor configured to:

acquire a transmission image of an inspected vehicle;

remove parts of the transmission image that are outside the inspected vehicle in the transmission image to obtain a transmission image of the inspected vehicle;

acquire a transmission image template of a vehicle model the same as that of the inspected vehicle from a database, perform registration on the transmission image of the inspected vehicle with the transmission image template to obtain a registered transmission image, determine a difference between the registered transmission image and the transmission image template to obtain a change area of the transmission image of the inspected vehicle relative to the transmission image template, and process the change area to determine whether the inspected vehicle carries a suspected object or not;

wherein the processor is further configured to:

remove strip in the transmission image of the inspected vehicle to obtain an image having a changing background;

obtain a gradient map for the image having the changing background and quantize the gradient map to obtain a binary quantized gradient map;

obtain a largest continuous region in a horizontal projection and a vertical projection in the binary quantized gradient map; and remove parts outside the largest continuous region in the transmission image of the vehicle to obtain the transmission image of inspected vehicle.

7. The vehicle inspection system according to claim 6, wherein the processor is further configured to:

extract information on an internal structure of the vehicle from the transmission image; and retrieve the transmission image template of the vehicle model from the database based on the information on the internal structure as well as information on external features of the vehicle.

8. The vehicle inspection method according to claim 1, wherein said performing registration on the transmission image of the inspected vehicle with the transmission image template comprises:

performing rigid registration on the transmission image of the inspected vehicle with the transmission image template to obtain a transmission image performed rigid registration; wherein the transmission image performed rigid registration is aligned with the transmission image template by a global transformation;

performing normalization on gray levels of the transmission image performed rigid registration; and performing elastic registration on the normalized transmission image performed rigid registration to obtain the registered transmission image without local deformation after the registration.

* * * * *